(12) United States Patent
Morikawa et al.

(10) Patent No.: US 11,124,743 B2
(45) Date of Patent: Sep. 21, 2021

(54) LIQUID DETERGENT COMPOSITION FOR TEXTILE PRODUCTS

(71) Applicant: KAO CORPORATION, Tokyo (JP)

(72) Inventors: Satoshi Morikawa, Wakayama (JP); Ayako Sakuraba, Wakayama (JP); Ayako Kusunoki, Wakayama (JP); Hiroko Endo, Tokyo (JP)

(73) Assignee: KAO CORPORATION, Tokyo (JP)

( * ) Notice: Subject to any disclaimer, the term of this patent is extended or adjusted under 35 U.S.C. 154(b) by 130 days.

(21) Appl. No.: 16/303,552

(22) PCT Filed: May 30, 2017

(86) PCT No.: PCT/JP2017/020063
§ 371 (c)(1),
(2) Date: Nov. 20, 2018

(87) PCT Pub. No.: WO2017/209120
PCT Pub. Date: Dec. 7, 2017

(65) Prior Publication Data
US 2020/0308512 A1   Oct. 1, 2020

(30) Foreign Application Priority Data
May 31, 2016   (JP) .............................. JP2016-108447

(51) Int. Cl.
| C11D 3/00 | (2006.01) |
| C11D 3/43 | (2006.01) |
| C11D 1/14 | (2006.01) |
| C11D 3/20 | (2006.01) |
| C11D 11/00 | (2006.01) |

(52) U.S. Cl.
CPC ............... *C11D 3/43* (2013.01); *C11D 1/14* (2013.01); *C11D 3/201* (2013.01); *C11D 3/2044* (2013.01); *C11D 3/2048* (2013.01); *C11D 3/2068* (2013.01); *C11D 11/0017* (2013.01)

(58) Field of Classification Search
None
See application file for complete search history.

(56) References Cited

U.S. PATENT DOCUMENTS

| 4,029,608 | A | 6/1977 | Murata et al. |
| 4,107,095 | A | 8/1978 | Klisch et al. |
| 4,507,223 | A | 3/1985 | Tano et al. |
| 4,549,607 | A | 10/1985 | Morita et al. |
| 5,078,916 | A * | 1/1992 | Kok ........................ C11D 1/143 510/488 |
| 2006/0277688 | A1 | 12/2006 | Ishikawa et al. |
| 2007/0203053 | A1 | 8/2007 | Torres et al. |
| 2009/0022812 | A1 | 1/2009 | Maki et al. |
| 2014/0076345 | A1 | 3/2014 | Fujii et al. |
| 2014/0079658 | A1 | 3/2014 | Terazaki et al. |
| 2014/0079660 | A1 | 3/2014 | Doi |
| 2014/0080746 | A1 | 3/2014 | Doi et al. |
| 2014/0336409 | A1 | 11/2014 | Barnes et al. |
| 2015/0202134 | A1* | 7/2015 | Yoshikawa ............ A61Q 19/10 510/127 |
| 2015/0275133 | A1 | 10/2015 | Doi |
| 2015/0366774 | A1 | 12/2015 | Yoshikawa et al. |
| 2015/0366775 | A1 | 12/2015 | Yoshikawa et al. |
| 2016/0332961 | A1 | 11/2016 | Hori et al. |
| 2017/0079899 | A1 | 3/2017 | Li et al. |
| 2017/0114270 | A1 | 4/2017 | Ravikiran et al. |

FOREIGN PATENT DOCUMENTS

| CA | 2026746 A1 | 4/1991 |
| CN | 104560283 A | 4/2015 |
| CN | 104603251 A | 5/2015 |
| CN | 105238573 A | 1/2016 |
| CN | 105255602 A | 1/2016 |
| CN | 105849085 A | 8/2016 |
| EP | 0377261 A2 | 7/1990 |
| EP | 0482687 A1 | 4/1992 |
| EP | 2 899 257 A1 | 7/2015 |
| EP | 2 899 258 A1 | 7/2015 |

(Continued)

OTHER PUBLICATIONS

International Preliminary Report on Patentability and English translation of the Written Opinion of the International Searching Authority (forms PCT/IB/373 and PCT/ISA/237), dated Dec. 4, 2018, for International Application No. PCT/JP2017/020059.

International Preliminary Report on Patentability and English translation of the Written Opinion of the International Searching Authority (forms PCT/IB/373 and PCT/ISA/237), dated Dec. 4, 2018, for International Application No. PCT/JP2017/020061.

International Preliminary Report on Patentability and English translation of the Written Opinion of the International Searching Authority (forms PCT/IB/373 and PCT/ISA/237), dated Dec. 4, 2018, for International Application No. PCT/JP2017/020063.

(Continued)

*Primary Examiner* — Necholus Ogden, Jr.
(74) *Attorney, Agent, or Firm* — Birch, Stewart, Kolasch & Birch, LLP.

(57) ABSTRACT

The present invention relates to a liquid detergent composition for textile products containing the following component (A) in an amount of 10% by mass or more and 60% by mass or less), the following component (B), and water:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and component (B): an organic solvent having a hydroxy group.

18 Claims, No Drawings

(56) References Cited

FOREIGN PATENT DOCUMENTS

| | | |
|---|---|---|
| EP | 3 088 386 A1 | 11/2016 |
| JP | 59-27995 A | 2/1984 |
| JP | 60-096693 A | 5/1985 |
| JP | 62-297400 A | 12/1987 |
| JP | 3-126793 A | 5/1991 |
| JP | 5-39212 A | 2/1993 |
| JP | 6-316700 A | 11/1994 |
| JP | 10-298597 A | 11/1998 |
| JP | 2001-247534 A | 9/2001 |
| JP | 2003-81935 A | 3/2003 |
| JP | 2011-32456 A | 2/2011 |
| JP | 2014-76988 A | 5/2014 |
| JP | 2014-77126 A | 5/2014 |
| JP | 2014-167107 A | 9/2014 |
| JP | 2014-177620 A | 9/2014 |
| JP | 2015-27977 A | 2/2015 |
| JP | 2015-28123 A | 2/2015 |
| JP | 2015-506340 A | 3/2015 |
| JP | 2015-143203 A | 8/2015 |
| JP | 2015-178466 A | 10/2015 |
| JP | 2015-178548 A | 10/2015 |
| RU | 2463339 C2 | 10/2012 |
| TW | 200517556 A | 6/2005 |
| TW | 200632091 A | 9/2006 |
| TW | 201414501 A | 4/2014 |
| WO | WO 2014/046176 A1 | 3/2014 |
| WO | WO 2015/098415 A1 | 7/2015 |

OTHER PUBLICATIONS

JP-2003-81935-A, published Mar. 19, 2003, with machine translation.
JP-60-96693-A, published May 30, 1985, with machine translation.
Nagayama et al., "Aspects in Chemistry of Fatty-acid Sulfonic Acid," Journal of Synthetic Organic Chemistry, Japan, vol. 29, No. 7, 1971, pp. 639-653 (18 pages total), with machine translation of pp. 639-640).
Chinese Office Action and Search Report dated Dec. 4, 2019, for corresponding Chinese Patent Application No. 201780033632.X, with partial translation.
International Search Report (PCT/ISA/210) issued in PCT/JP2017/020063, dated Jul. 25, 2017.
U.S. Appl. No. 16/303,354, filed Nov. 20, 2018, Not Yet Assigned.
U.S. Appl. No. 16/303,478, filed Nov. 20, 2018, Not Yet Assigned.
Extended European Search Report for European Application No. 17806669.2, dated Nov. 14, 2019.
Extended European Search Report for European Application No. 17806671.8, dated Nov. 19, 2019.
Extended European Search Report for European Application No. 17806673.4, dated Nov. 19, 2019.
International Search Report (PCT/ISA/210) issued in PCT/JP2017/020059, dated Jul. 4, 2017.
International Search Report (PCT/ISA/210) issued in PCT/JP2017/020061, dated Aug. 15, 2017.
Russian Office Action and Search Report for Russian Application No. 2018145760, dated Jun. 22, 2020, with English translation.
Taiwanese Office Action and Search Report for Taiwanese Application No. 106117935, dated Apr. 7, 2021.
Taiwanese Office Action and Search Report for Taiwanese Application No. 106117976, dated Apr. 7, 2021.
Japanese Office Action for Japanese Application No. 2017-106500, dated Mar. 9, 2021.
Japanese Office Action for Japanese Application No. 2017-106503, dated Mar. 16, 2021.

* cited by examiner

US 11,124,743 B2

LIQUID DETERGENT COMPOSITION FOR TEXTILE PRODUCTS

FIELD OF THE INVENTION

The present invention relates to a liquid detergent composition for textile products, and a method for producing a liquid detergent composition for textile products.

BACKGROUND OF THE INVENTION

Heretofore, an anionic surfactant, particularly an alkylbenzene sulfonate, a nonionic surfactant having an oxyalkylene group having 2 or 3 carbon atoms and an olefin sulfonate, particularly an internal olefin sulfonate obtained by using, as a raw material, an internal olefin having a double bond not at the end of an olefin chain but inside the olefin chain have been widely used as household and industrial detergent components.

JP-A 2015-28123 and JP-A 2014-77126 disclose an internal olefin sulfonate composition excellent in foamability and the like which contains an internal olefin sulfonate having 16 carbon atoms and an internal olefin sulfonate having 18 carbon atoms in a specific ratio and having a specific ratio of hydroxy form/olefin form. They describe that a solubilizing agent such as propylene glycol is used.

JP-A 2003-81935 discloses an internal olefin sulfonate characterized in that it is obtained by sulfonating, neutralizing and hydrolyzing an internal olefin having 8 to 30 carbon atoms in which the total percentage of double bonds present at position 2 is 20 to 95% and the cis/trans ratio is 1/9 to 6/4. As a prior art, an internal olefin sulfonate, in which the position of a double bond is described, is described.

EP-A 377261 discloses a detergent composition containing an internal olefin sulfonate, in which its β-hydroxy form is 25% or more, having an excellent detergent property. As a specific example, it describes a liquid laundry detergent containing monopropylene glycol.

JP-A 2011-32456 describes the use of a water-miscible organic solvent from the viewpoint of improving the stability and solubility of a liquid detergent composition.

SUMMARY OF THE INVENTION

The present invention relates to a liquid detergent composition for textile products which is excellent in the effect of imparting a texture to textile products and excellent in detergency against stains attached to textile products.

The present invention relates to a liquid detergent composition for textile products containing the following component (A) in an amount of 10% by mass or more and 60% by mass or less, the following component (B), and water:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and Component (B): an organic solvent having a hydroxy group.

In one aspect, the present invention relates to a liquid detergent composition for textile products containing the following component (A1) in an amount of 10% by mass or more and 60% by mass or less, the following component (B), and water:

component (A1): an internal olefin sulfonate obtained from an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) is 0.50 or more and 6.5 or less; and Component (B): an organic solvent having a hydroxy group.

In another aspect, the present invention relates to a liquid detergent composition for textile products containing the following component (A) in an amount of 10% by mass or more and 60% by mass or less, the following component (B), and water:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and wherein the internal olefin sulfonate is an internal olefin sulfonate obtained from an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) is 0.50 or more and 6.5 or less; and Component (B): an organic solvent having a hydroxy group.

The present invention also relates to a method for producing a liquid detergent composition for textile products, including mixing the following component (A), the following component (B) and water, wherein the percentage of component (A) in all components to be mixed is 10% by mass or more and 60% by mass or less:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and Component (B): an organic solvent having a hydroxy group.

According to the present invention, it is possible to provide a liquid detergent composition for textile products that can impart a texture to textile products while keeping the detergent property against stains attached to textile products.

EMBODIMENTS OF THE INVENTION

<Liquid Detergent Composition for Textile Products>

The present inventors have found that a liquid detergent composition for textile products containing an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-13)

to an internal olefin sulfonate having 17 or more and 24 or less carbon atoms with the sulfonate group at position 5 or higher (IO-2S), (IO-1S)/(IO-2S), is 0.75 or more and 5.5 or less; water; and an organic solvent having a hydroxy group is excellent in the effect of imparting a texture to textile products and excellent in detergency against stains attached to textile products.

The internal olefin sulfonate may be an internal olefin sulfonate obtained from an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) is 0.50 or more and 6.5 or less.

<Component (A)>

Component (A) of the present invention is an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less, and has the effect of washing off stains attached to fibers. Component (A) can also increase the effect of imparting a texture to textile products by using it in combination with component (B), an organic solvent having a hydroxy group described later. Particularly, the liquid detergent composition for textile products of the present invention can increase the effect of imparting a texture to fibers even when used for washing at a low temperature. Component (A) can be obtained by sulfonating an internal olefin having 17 or more and 24 or less carbon atoms. (IO-2S) is an internal olefin sulfonate having 17 or more and 24 or less carbon atoms with the sulfonate group at position 5 or higher and position 9 or lower.

Component (A) is an internal olefin sulfonate having 17 or more and 24 or less carbon atoms. In addition, component (A) contains an internal olefin sulfonate having 17 or more and 24 or less carbon atoms with the sulfonate group at position 2 or higher and position 4 or lower (IO-1S) and an internal olefin sulfonate having 17 or more and 24 or less carbon atoms with the sulfonate group at position 5 or higher (IO-2S), and the mass ratio of (IO-1S)/(IO-2S) is 0.75 or more and 5.5 or less.

(IO-1S)/(IO-2S) which is the mass ratio of the content of (IO-1S) to the content of (IO-2S) in component (A) is, from the viewpoint of improving the softness of fibers and from the viewpoint of improving the detergent property, 0.75 or more, more preferably 0.9 or more, further preferably 1.0 or more, furthermore preferably 1.2 or more, furthermore preferably 1.4 or more, furthermore preferably 1.6 or more, furthermore preferably 2.0 or more, furthermore preferably 2.4 or more and furthermore preferably 4.5 or more, and 5.5 or less.

The content of each of compounds with the sulfonate group at different positions in component (A) can be measured by a high performance liquid chromatography/mass spectrometer (hereinafter abbreviated as HPLC-MS). The content of each of compounds with the sulfonate group at different positions in the present specification will be determined as the mass ratio based the HPLC-MS peak area of the compound with the sulfonate group at each position in all HAS forms of component (A).

In the specification, HAS is a hydroxyalkane sulfonate, i.e., a hydroxy form of an internal olefin sulfonate, among compounds produced by sulfonating an internal olefin.

In the present invention, an internal olefin sulfonate having 17 or more and 24 or less carbon atoms with the sulfonate group at position 2 or higher and position 4 or less (IO-1S) refers to a sulfonate having 17 or more and 24 or less carbon atoms with the sulfonate group at position 2 or higher and position 4 or less, among HAS forms having 17 or more and 24 or less carbon atoms.

On the other hand, an internal olefin sulfonate having 17 or more and 24 or less carbon atoms with the sulfonate group at position 5 or higher (IO-2S) refers to a sulfonate having 17 or more and 24 or less carbon atoms with the sulfonate acid group at position 5 or higher, among HAS forms having 17 or more and 24 or less carbon atoms.

The internal olefin sulfonate which is component (A) includes and is composed of an internal olefin sulfonate having 17 or more and 24 or less carbon atoms with the sulfonate group at position 2 or higher and position 4 or lower (IO-1S) and an internal olefin sulfonate having 17 or more and 24 or less carbon atoms with the sulfonate group at position 5 or higher (IO-2S). The position at which the sulfonic acid group is bonded most frequently in the internal olefin sulfonate (IO-2S) varies depending on the number of carbon atoms.

The mass ratio (IO-1S)/(IO-2S) in component (A) is based on the component (A) finally obtained. For example, even if the internal olefin sulfonate is one obtained by mixing internal olefin sulfonates having the mass ratio (IO-1S)/(IO-2S) out of the above range, it corresponds to the internal olefin sulfonate of component (A) as long as the mass ratio (IO-1S)/(IO-2S) in the composition of the internal olefin sulfonate is in the above range.

The content of (IO-2S) in component (A) is, from the viewpoint of improving the softness of fibers, preferably 60% by mass or less, more preferably 54% by mass or less, further preferably 52% by mass or less, furthermore preferably 49% by mass or less, furthermore preferably 45% by mass or less, furthermore preferably 42% by mass or less, furthermore preferably 38% by mass or less, furthermore preferably 33% by mass or less, furthermore preferably 30% by mass or less and furthermore preferably 20% by mass or less, and from the viewpoint of ease of production, preferably more than 0% by mass and more preferably more than 5% by mass.

Examples of the salt of the internal olefin sulfonate include an alkali metal salt, an alkaline earth metal (1/2 atom) salt, an ammonium salt or an organic ammonium salt. Examples of the alkali metal salt include a sodium salt and a potassium salt. Examples of the organic ammonium salt include an alkanolammonium salt having 1 or more and 6 or less carbon atoms.

Component (A) of the present invention can be obtained by using as a raw material an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher, (IO-2), (IO-1)/(IO-2) is 0.50 or more and 6.5 or less.

The internal olefin used to obtain component (A) is composed of an olefin having 17 or more and 24 or less carbon atoms with a double bond at position 1 or higher and position 3 or lower (IO-1), an olefin having 17 or more and 24 or less carbon atoms with a double bond at position 4 and an olefin having 17 or more and 24 or less carbon atoms with a double bond at position 5 or higher (IO-2). The position at which the double bond occurs most frequently in the olefin (IO-2) varies depending on the number of carbon atoms.

From the viewpoint of keeping the effect of imparting a texture to fibers even when the liquid detergent composition for textile products of the present invention is used for washing at a low temperature, the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) in the internal olefin having 17 or more and 24 or less carbon atoms is preferably 6.5 or less, more preferably 6.0 or less, further preferably 5.5 or less, furthermore preferably 5.0 or less, furthermore preferably 4.5 or less, furthermore preferably 4.0 or less, furthermore preferably 3.5 or less, furthermore preferably 3.0 or less and furthermore preferably 2.5 or less, and preferably 0.50 or more, more preferably 0.60 or more and further preferably 0.65 or more.

From the viewpoint of improving the detergent property against stains attached to textile products, the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) in the internal olefin having 17 or more and 24 or less carbon atoms is preferably 0.50 or more, more preferably 0.65 or more, further preferably 0.70 or more, furthermore preferably 0.80 or more and furthermore preferably 0.85 or more, and preferably 6.5 or less, more preferably 6.0 or less and more preferably 5.5 or less.

In addition, from the viewpoint that the liquid detergent composition for textile products of the present invention can wash off more stains attached to textile products, (IO-1)/(IO-2) is preferably 0.50 or more, more preferably 0.60 or more, further preferably 0.65 or more, furthermore preferably 0.70 or more, furthermore preferably 0.80 or more and furthermore preferably 0.85 or more, and preferably 6.5 or less.

The mass ratio (IO-1)/(IO-2) in the internal olefin to obtain component (A) is based on the component (A) finally obtained. For example, even if the internal olefin sulfonate is one obtained by mixing internal olefin sulfonates obtained by using as a raw material olefins having the mass ratio (IO-1)/(IO-2) out of the above range, it can correspond to the internal olefin sulfonate of component (A) obtained by using a predetermined olefin as a raw material, as long as the mass ratio (IO-1)/(IO-2) in the composition of the olefin corresponding to the olefin as a raw material is in the above range.

From the viewpoint of improving the effect of imparting a texture to textile products, the number of carbon atoms of the olefin as a raw material for component (A) is 17 or more and preferably 18 or more, and 24 or less, preferably 22 or less, more preferably 20 or less and further preferably 19 or less.

The internal olefin as a raw material for component (A) includes those containing a trace amount of so-called alpha-olefin (hereinafter also referred to as α-olefin) in which the double bond is at the position 1 of the carbon chain. The content of the α-olefin in the internal olefin is, from the viewpoint that the liquid detergent composition for textile products can keep the effect of imparting a texture to fibers even when used for washing at a low temperature, preferably 10% by mass or less, more preferably 7% by mass or less, further preferably 5% by mass or less and furthermore preferably 3% by mass or less, and from the viewpoint of reducing production cost and improving productivity, preferably 0.01% by mass or more.

When an internal olefin is sulfonated, β-sultone is produced quantitatively, and a part of β-sultone is changed to γ-sultone and an olefin sulfonate, and further converted to a hydroxyalkane sulfonate and an olefin sulfonate in the process of neutralization and hydrolysis (e.g., J. Am. Oil Chem. Soc. 69, 39 (1992)). The hydroxy group of the resulting hydroxyalkane sulfonate is inside the alkane chain, and the double bond of the olefin sulfonate is inside the olefin chain. The resulting product contains mainly a mixture of these, and may contain, in some cases, a trace amount of a hydroxyalkane sulfonate having a hydroxy group at the end of its carbon chain or an olefin sulfonate having a double bond at the end of its carbon chain.

In the present specification, each of these products and a mixture thereof are collectively referred to as "internal olefin sulfonate" (component (A)). In addition, "hydroxyalkane sulfonate" is referred to as "hydroxy form of internal olefin sulfonate" ("HAS"), and "olefin sulfonate" as "olefin form of internal olefin sulfonate" (hereinafter also referred to "IOS").

The mass ratio of the compound in component (A) can be measured by HPLC-MS. Specifically, the mass ratio can be determined from the HPLC-MS peak area of component (A).

Distribution of a double bond in the internal olefin as a raw material can be measured, for example, by gas chromatograph mass spectrometer (hereinafter abbreviated as GC-MS). Specifically, each component different in the carbon chain length and the double bond position is precisely separated from each other by a gas chromatograph analyzer (hereinafter abbreviated as GC), and each component can be subjected to a mass spectrometer (hereinafter abbreviated as MS) to identify the double bond position, and the percentage of each component can be determined from its GC peak area. As the content of the olefin having a double bond at the particular position described above, the value determined from the GC peak area is used. In addition, the position distribution of the double bonds when mixing and using olefins having different number of carbon atoms is represented by the position distribution of double bonds in olefins having the same number of carbon atoms.

In the present specification, the position distribution of the double bonds of olefins as a raw material for internal olefin sulfonates when mixing and using a plurality of internal olefin sulfonates obtained from a plurality of olefins different in the position of the double bond as a raw material is calculated based on the position distribution of double bonds in olefins having the same number of carbon atoms.

<Component (B)>

Component (B) is an organic solvent having a hydroxy group, and generally used as a solubilizing agent. However, in the present invention, the use of component (B) in combination with component (A) can improve the effect of imparting a texture to textile products.

Component (B) is, from the viewpoint of improving the effect of imparting a texture to fibers by using it in combination with component (A) of the liquid detergent composition for textile products of the present invention, preferably an organic solvent having C Log P of −1.5 or more and 2 or less. C Log P used in the present invention is the value calculated by using ChemProperty of ChemBioDraw Ultra ver. 14.0, by PerkinElmer, Inc. The larger value of C log P represents the higher hydrophobicity.

From the viewpoint of improving the effect of imparting a texture to textile products even when the liquid detergent composition for textile products is used for washing at a low temperature, component (B) is an organic solvent having a hydroxy group and having C Log P of preferably −1.4 or more, more preferably −1.2 or more, further preferably −1 or more, furthermore preferably −0.8 or more, furthermore preferably −0.5 or more, furthermore preferably −0.1 or more, furthermore preferably 0 or more, furthermore preferably 0.2 or more, furthermore preferably 0.4 or more and furthermore preferably 0.6 or more, and preferably 2 or less, more preferably 1.8 or less, further preferably 1.7 or less, furthermore preferably 1.6 or less and furthermore preferably 1.5 or less.

From the viewpoint of improving the effect of imparting a texture to textile products even when the textile products are washed after directly applying thereto the liquid detergent composition for textile products of the present invention, component (B) is an organic solvent having a hydroxy group and having C Log P of preferably −1.4 or more, more preferably −1.2 or more, further preferably −1 or more, furthermore preferably −0.8 or more, furthermore preferably −0.5 or more, furthermore preferably −0.1 or more, furthermore preferably 0 or more, furthermore preferably 0.2 or more, furthermore preferably 0.4 or more and furthermore preferably 0.6 or more, and preferably 2 or less, more preferably 1.8 or less, further preferably 1.7 or less, furthermore preferably 1.6 or less and furthermore preferably 1.5 or less.

In terms of further increasing the effect of component (A) imparting a texture to textile products, component (B) is preferably one or more organic solvents selected from components (B1) to (B4):

component (B1): a monohydric alcohol having 2 or more and 6 or less carbon atoms;

component (B2): an alcohol having 2 or more and 12 or less carbon atoms and 2 or more and 12 or less hydroxy groups;

component (B3): an organic solvent having a hydrocarbon group with 1 or more and 8 or less carbon atoms, an ether group and a hydroxy group (provided that an aromatic group is excluded from the hydrocarbon group); and component (B4): an organic solvent having an optionally partially substituted aromatic group, an ether group and a hydroxy group.

Specific examples of components (B1) to (B4) are shown below. Each of the figures in parentheses is the value (C Log P) calculated by using ChemProperty of ChemBioDraw Ultra ver. 14.0, by PerkinElmer, Inc.

Examples of the monohydric alcohol having 2 or more and 6 or less carbon atoms which is component (B1) include ethanol (−0.24), 1-propanol (0.29), 2-propanol (0.07) and phenol (1.48).

Examples of the alcohol having 2 or more and 12 or less carbon atoms and 2 or more and 12 or less hydroxy groups which is component (B2) include ethylene glycol (−1.4), propylene glycol (−1.1), butylene glycol (−0.73), hexylene glycol (−0.02), diethylene glycol (−1.3), triethylene glycol (−1.5), tetraethylene glycol (−1.66), dipropylene glycol (−0.69), tripropylene glycol (−0.55) and glycerol (−1.5).

Examples of the organic solvent having a hydrocarbon group having 1 or more and 8 or less carbon atoms, an ether group and a hydroxy group which is component (B3) include diethylene glycol monomethyl ether (−0.78), diethylene glycol dimethyl ether (−0.26), triethylene glycol monomethyl ether (−0.96), diethylene glycol monoethyl ether (−0.39), diethylene glycol diethyl ether (0.52), diethylene glycol monobutyl ether (0.67), dipropylene glycol monomethyl ether (−0.16), dipropylene glycol monoethyl ether (0.23), tripropylene glycol monomethyl ether (−0.03), 1-methoxy-2-propanol (−0.30), 1-ethoxy-2-propanol (0.09), 1-methyl glycerol ether (−1.43), 2-methyl glycerol ether (−0.73), 1,3-dimethyl glycerol ether (−0.67), 1-ethyl glycerol ether (−1.04), 1,3-diethyl glycerol ether (0.11), triethyl glycerol ether (0.83), 1-pentyl glyceryl ether (0.54), 2-pentyl glyceryl ether (1.25), 1-octyl glyceryl ether (2.1) and 2-ethylhexyl glyceryl ether (2.0).

Examples of the organic solvent having an optionally partially substituted aromatic group, an ether group and a hydroxy group which is component (B4) include 2-phenoxyethanol (1.2), diethylene glycol monophenyl ether (1.25), triethylene glycol monophenyl ether (1.08), polyethylene glycol monophenyl ether having an average molecular weight of approximately 480 (not calculated), 2-benzyloxyethanol (1.1) and diethylene glycol monobenzyl ether (0.96).

Component (B) is preferably an organic solvent having a hydroxy group selected from component (B3) and component (B4) and having the above-mentioned C log P of 0.6 or more and 1.5 or less.

From the viewpoint of improving the softness of textile products even when the liquid detergent for textile products of the present invention is directly applied locally to the textile products, the percentage of the content of the organic solvent selected from component (B3) and component (B4) and having the C log P of 0.6 or more and 1.5 or less in the overall component (B) is preferably 40% by mass or more, more preferably 50% by mass or more and further preferably 60% by mass or more, and preferably 100% by mass or less.

<Water>

The liquid detergent composition for textile products of the present invention contains water. For example, in order to bring the composition of the present invention into a liquid state at 4° C. or more and 40° C. or less, water can be contained therein. Water to be used can be deionized water (sometimes also referred to as ion-exchanged water) or ion-exchanged water having sodium hypochlorite added at 1 mg/kg or more and 5 mg/kg or less thereto. Tap water can be also used.

<Fibers>

The fiber constituting textile products to be washed with the liquid detergent composition for textile products of the present invention may be either a hydrophobic fiber or a hydrophilic fiber. Examples of the hydrophobic fiber include a protein-based fiber (such as cow milk protein casein fiber or promix), a polyamide-based fiber (such as nylon), a polyester-based fiber (such as polyester), a polyacrylonitrile-based fiber (such as acrylic), a polyvinyl alcohol-based fiber (such as vinylon), a polyvinyl chloride-based fiber (such as polyvinyl chloride), a polyvinylidene chloride-based fiber (such as vinylidene), a polyolefin-based fiber (such as polyethylene or polypropylene), a polyurethane-based fiber (such as polyurethane), a polyvinyl chloride/polyvinyl alcohol copolymer-based fiber (such as polychlal), a polyalkylene paraoxybenzoate-based fiber (such as benzoate), a polyfluoroethylene-based fiber (such as polytetrafluoroethylene), a glass fiber, a carbon fiber, an alumina fiber, a silicon carbide fiber, a rock fiber, a slag fiber and a metal fiber (a gold thread, a silver thread or a steel fiber). Examples of the hydrophilic fiber include a seed hair fiber (such as cotton, arboreous cotton or kapok), a bast fiber (such as linen, flax, ramie, hemp or jute), vein fiber (such as manila hemp or sisal hemp), coconut fiber, rush, straw, an animal hair fiber (such as wool, mohair, cashmere, camel hair, alpaca, vicuna or angora), a silk fiber (domesticated silkworm silk or wild silkworm silk), a feather and down and a cellulosic fiber (such as rayon, polynosic, cupra or acetate).

The fiber is preferably a fiber containing a cotton fiber.

<Textile Product>

In the present invention, the textile product refers to a cloth produced by using the above-mentioned hydrophobic fiber or hydrophilic fiber such as a woven fabric, a knitted fabric or a nonwoven fabric, and a product obtained by using the cloth such as an undershirt, a T-shirt, a business shirt, a blouse, pants, a hat, a handkerchief, a towel, a knit, socks, an underwear or tights. From the viewpoint that the improvement effect of the texture of fibers after washing with the liquid detergent composition for textile products of the present invention is more easily felt, the textile product is preferably a textile product containing a cotton fiber. From the viewpoint of further improving the softness of fibers, the content of the cotton fiber in the textile product is preferably 5% by mass or more, more preferably 10% by mass or more, further preferably 15% by mass or more, furthermore preferably 20% by mass or more and furthermore preferably 100%.

<Composition and Others>

The content of component (A) in the liquid detergent composition for textile products of the present invention is, from the viewpoint of further improving the detergent property per mass of the liquid detergent composition for textile products when washing fibers, 10% by mass or more, preferably 11% by mass or more and more preferably 12% by mass or more, and from the viewpoint of further imparting more texture to textile products even when using the liquid detergent composition for textile products of the present invention for washing at a low temperature, 60% by mass or less, more preferably 50% by mass or less and further preferably 40% by mass or less.

The content of component (A) contained in the liquid detergent composition for textile products is based on the value calculated assuming that the counter ion is a sodium ion. That is, the content calculated based on the form of a sodium salt.

It is preferable in the present invention that the percentage of component (A) in all anionic surfactants contained in the liquid detergent composition for textile products is 50% by mass or more, further 60% by mass or more, further 70% by mass or more, further 80% by mass or more and further 90% by mass or more, and 100% by mass or less.

From the viewpoint of further improving the effect of imparting a texture to textile products, the content of component (B) in the liquid detergent composition for textile products of the present invention is preferably 4% by mass or more and more preferably 5% by mass or more, and preferably 40% by mass or less, more preferably 35% by mass or less, further preferably 30% by mass or less and furthermore preferably 25% by mass or less.

From the viewpoint of further improving the effect of imparting a texture to textile products, in the liquid detergent composition for textile products of the present invention, content of component (B)/content of component (A), which is the mass ratio of the content of component (B) to the content of component (A) is preferably 0.1 or more, more preferably 0.2 or more and further preferably 0.25 or more, and preferably 1 or less, more preferably 0.9% by mass or less, further preferably 0.8 or less and furthermore preferably 0.7 or less.

The content of water in the liquid detergent composition for textile products of the present invention is preferably 10% by mass or more and more preferably 15% by mass or more, and preferably 85% by mass or less and more preferably 80% by mass or less.

<Texture>

The texture in the present invention refers to the feeling such as softness, fluffy feeling or smoothness when touching textile products with the skin of the hand.

<Optional Components>

Surfactants other than component (A) can be used as component (C) in the liquid detergent composition for textile products of the present invention, as long as they do not interfere with the effect of the present invention. Examples of component (C) include one or more surfactants selected from anionic surfactants other than component (A) and nonionic surfactants.

Examples of component (C) include one or more surfactants selected from the following component (c1), component (c2), component (c3) and component (c4):

component (c1): alkyl or alkenyl sulfate, component (c2): polyoxyalkylene alkyl ether sulfate or polyoxyalkylene alkenyl ether sulfate, component (c3): an anionic surfactant having a sulfonate group (except for component (A)), and component (c4): a fatty acid or a salt thereof.

Specific examples of component (c1) include one or more anionic surfactants selected from alkyl sulfates having an alkyl group having 10 or more and 18 or less carbon atoms and alkenyl sulfates having an alkenyl group having 10 or more and 18 or less carbon atoms. From the viewpoint of improving the detergent property, component (c1) is preferably one or more anionic surfactants selected from alkyl sulfates having an alkyl group having 12 or more and 14 or less carbon atoms, and more preferably one or more anionic surfactants selected from sodium alkyl sulfates having an alkyl group having 12 or more and 14 or less carbon atoms.

Specific examples of component (c2) include one or more anionic surfactants selected from a polyoxyalkylene alkyl ether sulfate having an alkyl group having 10 or more and 18 or less carbon atoms and having an average number of moles of added alkylene oxide of 1 or more and 3 or less, and a polyoxyalkylene alkenyl ether sulfate having an alkenyl group having 10 or more and 18 or less carbon atoms and having an average number of moles of added alkylene oxide of 1 or more and 3 or less. From the viewpoint of improving the detergent property, component (c2) is preferably a polyoxyethylene alkyl sulfate having an average mole number of ethylene oxide added of 1 or more and 2.2 or less, more preferably a polyoxyethylene alkyl sulfate having an alkyl group having 12 or more and 14 or less carbon atoms and having an average number of moles of added ethylene oxide of 1 or more and 2.2 or less, and further preferably a sodium salt thereof.

An anionic surfactant having a sulfonate group as component (c3) refers to an anionic surfactant having a sulfonate as a hydrophilic group (except for component (A)).

Specific examples of component (c3) include one or more anionic surfactants selected from an alkylbenzene sulfonate having an alkyl group having 10 or more and 18 or less carbon atoms, an alkenylbenzene sulfonate having an alkenyl group having 10 or more and 18 or less carbon atoms, an alkane sulfonate having an alkyl group having 10 or more and 18 or less carbon atoms, an α-olefin sulfonate having an α-olefin moiety having 10 or more and 18 or less carbon atoms, an α-sulfofatty acid salt having a fatty acid moiety having 10 or more and 18 or less carbon atoms, and an α-sulfofatty acid lower alkyl ester salt having a fatty acid moiety having 10 or more and 18 or less carbon atoms and an ester moiety having 1 or more and 5 or less carbon atoms, and an internal olefin sulfonate having 12 or more and 16 or less carbon atoms. From the viewpoint of improving the detergent property, component (c3) is preferably an alkylbenzene sulfonate having an alkyl group having 11 or more and 14 or less carbon atoms, and more preferably a sodium alkylbenzene sulfonate having an alkyl group having 11 or more and 14 or less carbon atoms.

Examples of a fatty acid or a salt thereof as component (c4) include a fatty acid or a salt thereof having 10 or more and 20 or less carbon atoms. From the viewpoint of further increasing the effect of softening fibers of component (A), the number of carbon atoms of component (c4) is 10 or more, preferably 12 or more and more preferably 14 or more, and 20 or less and preferably 18 or less.

The salt of an anionic surfactant as components (c1) to (c4) is preferably an alkali metal salt, more preferably a sodium salt or a potassium salt, and further preferably a sodium salt.

In addition, examples of component (C) other than those described above include component (c5) which is a nonionic surfactant having a hydroxy group or polyoxyalkylene group.

In addition to these components, the following components (d1) to (d7) may be blended into the liquid detergent composition for textile products of the present invention:

(d1) 0.01% by mass or more and 10% by mass or less in the composition of an anti-stain redeposition agent and a dispersing agent such as polyacrylic acid, polymaleic acid or carboxymethyl cellulose, (d2) 0.01% by mass or more and 10% by mass or less in the composition of a bleaching agent such as hydrogen peroxide, sodium percarbonate or sodium perborate, (d3) 0.01% by mass or more and 10% by mass or less in the composition of a bleaching activator such as tetraacetylethylenediamine or bleaching activators represented by the general formulas (I-2) to (1-7) described in JP-A 6-316700, (d4) 0.001% by mass or more, preferably 0.01% by mass or more, more preferably 0.1% by mass or more and further preferably 0.3% by mass or more, and 2% by mass or less and preferably 1% by mass or less in the composition of one or more enzymes selected from cellulase, amylase, pectinase, protease and lipase and preferably one or more enzymes selected from amylase and protease, (d5) 0.001% by mass or more and 1% by mass or less in the composition of a fluorescent dye such as a fluorescent dye commercially available as a Tinopal CBS (trade name, manufactured by Ciba Specialty Chemicals) or Whitex SA (trade name, manufactured by Sumitomo Chemical Co., Ltd.), (d6) 0.01% by mass or more and 2% by mass or less in the composition of an antioxidant such as butylhydroxytoluene, distyrenated cresol, sodium sulfite or sodium hydrogen sulfite, and (d7) an appropriate amount of a pigment, a perfume, an antimicrobial preservative or a defoaming agent such as silicone.

The pH of the liquid detergent composition for textile products of the present invention at 20° C. is preferably 3 or more and more preferably 4 or more, and preferably 10 or less, more preferably 9 or less and further preferably 8 or less. The pH is measured according to the method for measuring pH described below.

<pH Measurement Method>

A pH measuring composite electrode (glass fitting sleeve-type, manufactured by HORIBA, Ltd.) is connected to a pH meter (pH/ion meter F-23, manufactured by HORIBA, Ltd.) and the power is turned on. A saturated potassium chloride aqueous solution (3.33 mol/L) is used as an internal liquid for pH electrode. Next, each of a pH 4.01 standard solution (a phthalate standard solution), a pH 6.86 standard solution (a neutral phosphate standard solution) and a pH 9.18 standard solution (a borate standard solution) is filled in a 100 mL beaker, and immersed in a thermostat bath at 25° C. for 30 minutes. The pH measuring electrode is immersed for 3 minutes in each of the standard solutions adjusted to a constant temperature, and subjected to calibration operation in the order of pH 6.86→pH 9.18→pH 4.01. Each of samples to be measured is adjusted to 25° C., the electrode of the pH meter is immersed in the sample, and the pH after 1 minute is measured.

The present invention provides a method for washing textile products, including washing the textile products with a detergent liquid containing a liquid detergent composition for textile products of the present invention and water. The matters described with respect to a liquid detergent composition for textile products of the present invention can be appropriately applied to this washing method. The content of component (A) in the detergent liquid is preferably 0.005% by mass or more and more preferably 0.01% by mass or more, and preferably 1% by mass or less and more preferably 0.8% by mass or less. In addition, the content of component (B) in the detergent liquid is preferably 0.001% by mass or more and more preferably 0.002% by mass or more, and preferably 0.6% by mass or less and more preferably 0.5% by mass or less.

The water used for the method for washing textile products of the present invention is preferably water having a hardness. From the viewpoint of further improving the effect of imparting a texture to textile products, the hardness of water is by German hardness, preferably 1° dH or more, more preferably 2° dH or more, further preferably 3.5° dH or more, furthermore preferably 5° dH or more and furthermore preferably 7° dH or more, and preferably 20° dH or less, more preferably 18° dH or less and further preferably 15° dH or less. The German hardness (° dH) used in the present specification refers to the concentration of calcium and magnesium in water expressed as the concentration calculated based on the form of $CaCO_3$: 1 mg/L (ppm) =about 0.056° dH (1° dH=17.8 ppm).

The concentrations of calcium and magnesium for this German hardness are determined by a chelate titration method using disodium ethylenediaminetetraacetate salt.

A specific method for measuring the German hardness of water in the present specification is shown as follows.

<Method for Measuring German Hardness of Water>

[Reagent]

0.01 mol/l EDTA.2Na solution: a 0.01 mol/l aqueous solution of disodium ethylenediaminetetraacetate (a titration solution, 0.01 M EDTA-Na2, manufactured by SIGMA-ALDRICH)

Universal BT indicator (product name: Universal BT, manufactured by Dojindo Laboratories)

Ammonia buffer solution for hardness measurement (a solution prepared by dissolving 67.5 g of ammonium chloride in 570 ml of 28 w/v % ammonia water and adding ion-exchanged water until the total volume is 1000 ml)

[Measurement of Hardness]

(1) 20 ml of water serving as a sample is collected in a conical beaker with a whole pipette.

(2) 2 ml of an ammonia buffer solution for hardness measurement is added thereto.

(3) 0.5 ml of Universal BT indicator is added thereto. It is made sure that the solution after addition is reddish violet.

(4) While shaking the conical beaker well, a 0.01 mol/l EDTA.2Na solution is added dropwise thereto from a burette, and the point at which the sample water turns blue is taken as the end point of the titration. (5) The total hardness is determined by the following calculation formula:

Hardness (° dH)=$T \times 0.01 \times F \times 56.0774 \times 100/A$ wherein:
T: Titer of a 0.01 mol/l EDTA.2Na solution (mL),
A: Sample volume (20 mL, a volume of sample water), and
F: Factor of a 0.01 mol/l EDTA.2Na solution.

The detergent liquid used in the present invention is preferably a detergent liquid obtained by mixing component (A), component (B), and water having a German hardness of 1° dH or more and 20° dH or less.

In the method for washing textile products of the present invention, the value of the bath ratio expressed as the ratio of the amount (liter) of a detergent liquid to the mass (kg) of textile products, that is, the amount (liter) of the detergent liquid/the mass (kg) of textile products (hereinafter sometimes also referred to as "bath ratio") is preferably 2 or more, more preferably 3 or more, further preferably 4 or more and furthermore preferably 5 or more, and preferably 100 or less.

In the method for washing textile products of the present invention, the time to wash textile products is, from the viewpoint of further improving the effect of imparting a texture to textile products, preferably 1 minute or more, more preferably 2 minutes or more and further preferably 3 minutes or more, and preferably 12 hours or less, more preferably 8 hours or less, further preferably 6 hours or less, furthermore preferably 3 hours or less and furthermore preferably 1 hour or less.

The method for washing textile products of the present invention is also suitable for a rotary washing method. The rotary washing method refers to a washing method in which textile products not fixed to a rotating device rotate together with the detergent liquid around the rotation axis. The rotary washing method can be carried out by a rotary type washing machine. Specific examples of the rotary type washing machine include a drum type washing machine, a pulsator type washing machine or an agitator type washing machine. As these rotary type washing machines, machines commercially available for household can be used, respectively. In terms of being able to reduce the amount of water used for one washing, drum type washing machines have recently become rapidly widespread. The drum type washing machines can reduce the amount of water used particularly during washing.

<Method for Producing Liquid Detergent Composition for Textile Products>

The present invention provides a method for producing a liquid detergent composition for textile products, including mixing the following component (A), the following component (B) and water, wherein the percentage of component (A) in all components to be mixed is 10% by mass or more and 60% by mass or less:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and component (B): an organic solvent having a hydroxy group.

Preferred embodiments of component (A) and component (B) in this production method are the same as those in the liquid detergent composition for textile products of the present invention. The matters described with respect to a liquid detergent composition for textile products of the present invention can be appropriately applied to this production method. The content in the composition described above can be replaced with the percentage in all components to be mixed.

The present invention also provides a method for producing a liquid detergent composition for textile products, including mixing the following component (A1), the following component (B) and water, wherein the percentage of component (A1) in all components to be mixed is 10% by mass or more and 60% by mass or less:

component (A1): an internal olefin sulfonate obtained from an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) is 0.50 or more and 6.5 or less; and component (B): an organic solvent having a hydroxy group.

Component (A1) in this production method may correspond to component (A). In that case, preferred embodiments of component (A) and component (B) are the same as those in the liquid detergent composition for textile products of the present invention. In addition, the matters described with respect to a liquid detergent composition for textile products of the present invention can be appropriately applied to this production method. The content in the composition described above can be replaced with the percentage in all components to be mixed.

EMBODIMENTS OF THE PRESENT INVENTION

Embodiments of the present invention will be illustrated as follows. The matters described with respect to a liquid detergent composition for textile products and a method for producing a liquid detergent composition for textile products of the present invention can be appropriately applied to these embodiments.

<1>

A liquid detergent composition for textile products containing the following component (A) in an amount of 10% by mass or more and 60% by mass or less, the following component (B), and water:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and component (B): an organic solvent having a hydroxy group.

<2>

The liquid detergent composition for textile products according to <1>, wherein (IO-2S) is an internal olefin sulfonate having 17 or more and 24 or less carbon atoms with the sulfonate group at position 5 or higher and position 9 or lower.

<3>

The liquid detergent composition for textile products according to <1> or <2>, wherein (IO-1S)/(IO-2S) which is the mass ratio of the content of (IO-1S) to the content of (IO-2S) in component (A) is 0.75 or more, preferably 0.9 or more, more preferably 1.0 or more, further preferably 1.2 or more, furthermore preferably 1.4 or more, furthermore preferably 1.6 or more, furthermore preferably 2.0 or more, furthermore preferably 2.4 or more and furthermore preferably 4.5 or more, and 5.5 or less.

<4>

The liquid detergent composition for textile products according to any one of <1> to <3>, wherein the content of (IO-2S) in component (A) is preferably 60% by mass or less, more preferably 54% by mass or less, further preferably 52% by mass or less, furthermore preferably 49% by mass or less, furthermore preferably 45% by mass or less, furthermore preferably 42% by mass or less, furthermore preferably 38% by mass or less, furthermore preferably 33% by mass or less, furthermore preferably 30% by mass or less and furthermore preferably 20% by mass or less, and preferably more than 0% by mass and more preferably 5% by mass or more.

<5>

The liquid detergent composition for textile products according to any one of <1> to <4>, wherein the percentage of component (A) in all anionic surfactants contained in the liquid detergent composition for textile products is 60% by mass or more and 100% by mass or less.

<6>

The liquid detergent composition for textile products according to any one of <1> to <5>, wherein the percentage of component (A) in all anionic surfactants contained in the liquid detergent composition for textile products is 70% by mass or more, further 80% by mass or more and further 90% by mass or more, and 100% by mass or less.

<7>

The liquid detergent composition for textile products according to any one of <1> to <6>, wherein the content of component (B) is preferably 4% by mass or more and more preferably 5% by mass or more, and preferably 40% by mass or less, more preferably 35% by mass or less, further preferably 30% by mass or less and furthermore preferably 25% by mass or less.

<8>

The liquid detergent composition for textile products according to any one of <1> to <7>, wherein content of component (B)/content of component (A), which is the mass ratio of the content of component (B) to the content of component (A) is preferably 0.1 or more, more preferably 0.2 or more and further preferably 0.25 or more, and preferably 1 or less, more preferably 0.9% by mass or less, further preferably 0.8 or less and furthermore preferably 0.7 or less.

<9>

The liquid detergent composition for textile products according to any one of <1> to <8>, wherein component (B) is one or more selected from the following components (B1) to (B4):

component (B1): a monohydric alcohol having 2 or more and 6 or less carbon atoms;

component (B2): an alcohol having 2 or more and 12 or less carbon atoms and 2 or more and 12 or less hydroxy groups;

component (B3): an organic solvent having a hydrocarbon group with 1 or more and 8 or less carbon atoms, an ether group and a hydroxy group (provided that an aromatic group is excluded from the hydrocarbon group); and component (B4): an organic solvent having an optionally partially substituted aromatic group, an ether group and a hydroxy group.

<10>

The liquid detergent composition for textile products according to any one of <1> to <9>, wherein C log P of component (B) is −1.5 or more and 2 or less.

<11>

The liquid detergent composition for textile products according to any one of <1> to <10>, wherein component (B) is an organic solvent having a hydroxy group and having C Log P of preferably −1.4 or more, more preferably −1.2 or more, further preferably −1 or more, furthermore preferably −0.8 or more, furthermore preferably −0.5 or more, furthermore preferably −0.1 or more, furthermore preferably 0 or more, furthermore preferably 0.2 or more, furthermore preferably 0.4 or more and furthermore preferably 0.6 or more, and preferably 2 or less, more preferably 1.8 or less, further preferably 1.7 or less, furthermore preferably 1.6 or less and furthermore preferably 1.5 or less.

<12>

The liquid detergent composition for textile products according to any one of <9> to <11>, wherein the percentage of the content of the organic solvent selected from component (B3) and component (B4) and having the C log P of 0.6 or more and 1.5 or less in the overall component (B) is preferably 40% by mass or more, more preferably 50% by mass or more and further preferably 60% by mass or more, and preferably 100% by mass or less.

<13>

The liquid detergent composition for textile products according to any one of <1> to <12>, wherein the content of water is preferably 10% by mass or more and more preferably 15% by mass or more, and preferably 85% by mass or less and more preferably 80% by mass or less.

<14>

A method for producing a liquid detergent composition for textile products, including mixing the following component (A), the following component (B) and water, wherein the percentage of component (A) in all components to be mixed is 10% by mass or more and 60% by mass or less:

component (A): an internal olefin sulfonate having 17 or more and 24 or less carbon atoms, wherein the mass ratio of an internal olefin sulfonate having 17 or more and 24 or less carbon atoms with the sulfonate group at position 2 or higher and position 4 or lower (IO-1S) to an internal olefin sulfonate having 17 or more and 24 or less carbon atoms with the sulfonate group at position 5 or higher (IO-2S), (IO-1S)/(IO-2S), is 0.75 or more and 5.5 or less; and component (B): an organic solvent having a hydroxy group.

<15>

A method for producing a liquid detergent composition for textile products, including mixing the following component (A1), the following component (B) and water, wherein the percentage of component (A1) in all components to be mixed is 10% by mass or more and 60% by mass or less:

component (A1): an internal olefin sulfonate obtained from an internal olefin having 17 or more and 24 or less carbon atoms, wherein the mass ratio of an olefin having 17 or more and 24 or less carbon atoms with a double bond at position 1 or higher and position 3 or lower (IO-1) to an olefin having 17 or more and 24 or less carbon atoms with a double bond at position 5 or higher (IO-2), (IO-1)/(IO-2) is 0.50 or more and 6.5 or less; and component (B): an organic solvent having a hydroxy group.

<16>

The method for producing a liquid detergent composition for textile products according to <15>, wherein the mass ratio of the olefin having 17 or more and 24 or less carbon atoms and having a double bond at position 1 or higher and position 3 or lower (IO-1) to the olefin having 17 or more and 24 or less carbon atoms and having a double bond at position 5 or higher (IO-2), (IO-1)/(IO-2) in the internal olefin having 17 or more and 24 or less carbon atoms is preferably 6.5 or less, more preferably 6.0 or less, further preferably 5.5 or less, furthermore preferably 5.0 or less, furthermore preferably 4.5 or less, furthermore preferably 4.0 or less, furthermore preferably 3.5 or less, furthermore preferably 3.0 or less and furthermore preferably 2.5 or less, and preferably 0.50 or more, more preferably 0.60 or more and further preferably 0.65 or more.
<17>
A method for washing textile products, including washing the textile products with a detergent liquid containing the liquid detergent composition for textile products according to any one of <1> to <13>, and water.
<18>
The method for washing textile products according to <17>, wherein the content of component (A) in the detergent liquid is preferably 0.005% by mass or more and more preferably 0.01% by mass or more, and preferably 1.0% by mass or less and more preferably 0.8% by mass or less.
<19>
The method for washing textile products according to <17> or <18>, wherein the content of component (B) in the detergent liquid is preferably 0.001% by mass or more and more preferably 0.002% by mass or more, and preferably 0.8% by mass or less and more preferably 0.5% by mass or less.

EXAMPLES

<Preparation of Component (A)>
(1) Synthesis of Internal Olefins A to C (Production Examples A to C)
Internal olefins A to C which are raw materials of component (A) and component (A') (a comparative component of component (A)) were synthesized as follows.
7000 g (25.9 mol) of 1-octadecanol (product name: KAL-COL 8098, manufactured by Kao Corporation) and 700 g of γ-alumina (Strem Chemicals, Inc.) as a solid acid catalyst were introduced into a flask equipped with a stirring device, and allowed to react at 280° C. with stirring for a different reaction time for each of Production Examples A to C while passing nitrogen (7000 mL/min) through the system. The resulting crude internal olefin was transferred to a distillation flask and subjected to distillation at 148 to 158° C./0.5 mmHg to obtain each of internal olefins A to C having 18 carbon atoms at an olefin purity of 100%. The double bond distribution of each of the obtained internal olefins is shown in Table 1.
(2) Internal Olefin D Having 16 Carbon Atoms
An internal olefin obtained by using the method described in Production Example C of JP-A 2014-76988 was used as an internal olefin D having 16 carbon atoms. The double bond distribution of the obtained internal olefin D is shown in Table 1.

TABLE 1

| | Internal olefin | | | |
| --- | --- | --- | --- | --- |
| | A | B | C | D |
| Number of carbon atoms of hydrocarbon group | 18 | 18 | 18 | 16 |

TABLE 1-continued

| | | Internal olefin | | | |
| --- | --- | --- | --- | --- | --- |
| | | A | B | C | D |
| Distribution of (IO-1) | Position 1 | 1.6 | 0.9 | 0.3 | 0.5 |
| double bond | Position 2 | 41.7 | 25.0 | 13.3 | 30.1 |
| in linear olefin | Position 3 | 29.3 | 21.9 | 12.6 | 25.5 |
| (% by mass) | Position 4 | 15.7 | 19.0 | 13.9 | 18.8 |
| (IO-2) | Position 5 | 6.3 | 13.6 | 14.8 | 11.1 |
| | Position 6 | 3.9 | 8.6 | 13.7 | 7.0 |
| | Position 7 | 1.1 | 5.6 | 12.6 | 3.5 |
| | Position 8 | 0.2 | 2.7 | 9.4 | 3.5 |
| | Position 9 | 0.2 | 2.7 | 9.4 | 0.0 |
| (IO-1)/(IO-2) (mass ratio) | | 6.2 | 1.4 | 0.44 | 2.2 |

The double bond distribution of each of the internal olefins was measured by gas chromatography (hereinafter abbreviated as GC). Specifically, the internal olefin was reacted with dimethyl disulfide to form its dithiolated derivative, and then each component was subjected to separation by GC. The double bond distribution of internal olefin was determined from each of the resulting peak areas. For the olefins having 18 carbon atoms, the internal olefin with a double bond at position 8 and the internal olefin with a double bond at position 9 cannot be distinguished from each other in structure but distinguished when they are sulfonated. Therefore, the value obtained by dividing the amount of the internal olefin with a double bond at position 8 by 2 is conveniently shown in each of the columns for positions 8 and 9. Similarly, for the olefins having 16 carbon atoms, the value obtained by dividing the amount of the internal olefin with a double bond at position 7 by 2 is conveniently shown in each of the columns for positions 7 and 8.
The devices and the analysis conditions used for the measurement are as follows: a GC system: "HP6890" (manufactured by Hewlett-Packard Company); a column: "Ultra-Alloy-1 HT Capillary Column" (30 m×250 μm×0.15 μm, manufactured by Frontier Laboratories, Ltd.); a detector (hydrogen flame ionization detector (FID)); injection temperature: 300° C.; detector temperature: 350° C.; and He flow rate: 4.6 mL/min.
(3) Synthesis of (a-1), (a-4), (a-1') and (a'-2)
Each of internal olefins A to D was subjected to sulfonation reaction by passing sulfur trioxide gas therethrough using a thin film-type sulfonation reactor equipped with an external jacket while passing cooling water at 20° C. through the external jacket. The molar ratio of $SO_3$/the internal olefin during the sulfonation reaction was set at 1.09. The resulting sulfonated product was added to an alkaline aqueous solution which had been prepared using sodium hydroxide in an amount of 1.5 molar times the theoretical acid value, and the mixture was neutralized at 30° C. for 1 hour while being stirred. The neutralized product was hydrolyzed by being heated in an autoclave at 160° C. for 1 hour to obtain a crude product of each sodium internal olefin sulfonate. 300 g of the crude product was transferred to a separating funnel, 300 mL of ethanol was added thereto and petroleum ether in an amount of 300 mL per time was then added thereto to extract and remove oil-soluble impurities. At this time, inorganic compounds (mainly including sodium sulfate decahydrate) which precipitated at the oil/water interface by the addition of ethanol was also separated and removed from the aqueous phase by oil-water separation operation. This extraction and removal operation was carried out three times. The aqueous phase was evaporated to dryness to obtain each of the following sodium internal olefin sulfonates. The internal olefin sulfonate obtained by using internal olefin A as a raw material is referred to as a component (a-1), the internal olefin sulfonate obtained by using internal olefin B as a raw material is referred to as a component (a-4), the internal olefin sulfonate obtained by using internal olefin C as a raw material is referred to as a component (a'-1), and the internal olefin sulfonate obtained by using internal olefin D as a raw material is referred to as a component (a'-2).

The percentage of the content of the internal olefin sulfonate with the sulfonate group attached thereto of each component was measured by high performance liquid chromatography/mass spectrometer (HPLC-MS). Specifically, identification was carried out by separating the hydroxy form with the sulfonate group attached thereto by high performance liquid chromatography (HPLC) and subjecting it to mass spectrometer (MS). Each percentage was determined from the resulting HPLC-MS peak area. In the present specification, each percentage determined from the peak area was calculated as percentage by mass.

The devices and the analysis conditions used for the measurement are as follows: an HPLC device: "LC-20ASXR" (manufactured by Shimadzu Corporation); a column: "ODS Hypersil®" (4.6×250 mm, particle size: 3 μm, manufactured by Thermo Fisher Scientific K.K.); sample preparation (1000 times diluted with methanol); eluent A (10 mM ammonium acetate-added water); eluent B (a 10 mM ammonium acetate-added methacrylonitrile/water=95/5 (v/v) solution); gradient (0 minute (A/B=60/40)→15.1 to 20 minutes (30/70)→20.1 to 30 minutes (60/40); an MS device "LCMS-2020" (manufactured by Shimadzu Corporation); ESI detection (negative ion detection, m/z: 349.15 (component (A) or component (A') having 18 carbon atoms), 321.10 (component (A') having 16 carbon atoms); column temperature (40° C.); flow rate (0.5 mL/min); and injection volume (5 μL).

The distribution of the positions of the carbon through which each of sulfonate groups of (a-1), (a-4), (a'-1) and (a'-2) obtained is attached is shown in Table 2.

TABLE 2

|  |  | Component (A) | | Component (A') | |
|---|---|---|---|---|---|
|  |  | (a-1) | (a-4) | (a'-1) | (a'-2) |
| Number of carbon atoms of hydrocarbon group | | 18 | 18 | 18 | 16 |
| Distribution of sulfonate group (% by mass) | Position 1 (IO-1S) | 1.6 | 1.4 | 0.6 | 1.5 |
| | Position 2 | 31.5 | 22.1 | 12.8 | 24.1 |
| | Position 3 | 25.1 | 17.2 | 10.7 | 19.9 |
| | Position 4 | 24.7 | 21.8 | 16.6 | 24.6 |
| | Positions 5 to 9 (IO-2S) | 17.1 | 37.5 | 59.3 | 29.9 |
| (IO-1S)/(IO-2S) (mass ratio) | | 4.8 | 1.6 | 0.68 | 2.3 |

(4) Preparation of Component (A) Other than Described Above (A-1) and (a-4) were mixed to prepare (a-2) and (a-3). In addition, (a-4) and (a'-1) were mixed to prepare (a-5) and (a-9).

The double bond distribution of the internal olefins which are a raw material for (a-1) to (a-9), and (a'-1) and (a'-2) obtained is shown in Table 3.

In addition, the position distribution of the carbon through which each of sulfonate groups of (a-1) to (a-9), and (a'-1) and (a'-2) obtained is attached is shown in Table 4.

Some sodium internal olefin sulfonates are shown below.

(a-1): a sodium internal olefin sulfonate obtained from internal olefin A

The mass ratio of the hydroxy form (sodium hydroxyalkane sulfonate)/the olefin form (sodium olefin sulfonate) in the sodium internal olefin sulfonate: 82/18

(a-4): a sodium internal olefin sulfonate obtained from internal olefin B

The mass ratio of the hydroxy form (sodium hydroxyalkane sulfonate)/the olefin form (sodium olefin sulfonate) in the sodium internal olefin sulfonate: 83/17

(a'-1): a sodium internal olefin sulfonate obtained from internal olefin C

The mass ratio of the hydroxy form (sodium hydroxyalkane sulfonate)/the olefin form (sodium olefin sulfonate) in the sodium internal olefin sulfonate: 83/17

(a'-2): a sodium internal olefin sulfonate obtained from internal olefin D

The mass ratio of the hydroxy form (sodium hydroxyalkane sulfonate)/the olefin form (sodium olefin sulfonate) in the sodium internal olefin sulfonate: 84/16

TABLE 3

|  |  | Component (A) | | | | | | | | | Component (A') | |
|---|---|---|---|---|---|---|---|---|---|---|---|---|
|  |  | (a-1) | (a-2) | (a-3) | (a-4) | (a-5) | (a-6) | (a-7) | (a-8) | (a-9) | (a'-1) | (a'-2) |
| Number of carbon atoms of olefin as raw material | | 18 | 18 | 18 | 18 | 18 | 18 | 18 | 18 | 18 | 18 | 16 |
| Distribution of double bond in olefin as raw material (IO-1) (% by mass) | Position 1 | 1.6 | 1.2 | 1.0 | 0.9 | 0.8 | 0.7 | 0.6 | 0.5 | 0.4 | 0.3 | 0.5 |
| | Position 2 | 41.7 | 31.7 | 28.4 | 25.0 | 23.1 | 21.1 | 19.2 | 17.2 | 15.3 | 13.3 | 30.1 |
| | Position 3 | 29.3 | 24.9 | 23.4 | 21.9 | 20.4 | 18.8 | 17.3 | 15.7 | 14.1 | 12.6 | 25.5 |
| | Position 4 | 15.7 | 17.6 | 18.4 | 19.0 | 18.1 | 17.4 | 16.5 | 15.6 | 14.7 | 13.9 | 18.8 |
| (IO-2) | Position 5 | 6.3 | 10.7 | 12.1 | 13.6 | 13.8 | 14.0 | 14.2 | 14.4 | 14.6 | 14.8 | 11.1 |
| | Position 6 | 3.9 | 6.7 | 7.6 | 8.6 | 9.4 | 10.3 | 11.1 | 12.0 | 12.9 | 13.7 | 7.0 |
| | Position 7 | 1.1 | 3.8 | 4.7 | 5.6 | 6.8 | 7.9 | 9.1 | 10.2 | 11.4 | 12.6 | 3.5 |
| | Position 8 | 0.2 | 1.7 | 2.2 | 2.7 | 3.8 | 4.9 | 6.0 | 7.2 | 8.3 | 9.4 | 3.5 |
| | Position 9 | 0.2 | 1.7 | 2.2 | 2.7 | 3.8 | 4.9 | 6.0 | 7.2 | 8.3 | 9.4 | 0.0 |
| Total | | 100.0 | 100.0 | 100.0 | 100.0 | 100.0 | 100.0 | 100.0 | 100.0 | 100.0 | 100.0 | 100.0 |
| (IO-1)/(IO-2) of olefin as raw material (mass ratio) | | 6.2 | 2.4 | 1.8 | 1.4 | 1.2 | 0.97 | 0.80 | 0.66 | 0.54 | 0.44 | 2.2 |

TABLE 4

| | | | Component (A) | | | | | | | | | Component (A') | |
|---|---|---|---|---|---|---|---|---|---|---|---|---|---|---|
| | | | (a-1) | (a-2) | (a-3) | (a-4) | (a-5) | (a-6) | (a-7) | (a-8) | (a-9) | (a'-1) | (a'-2) |
| Number of carbon atoms | | | 18 | 18 | 18 | 18 | 18 | 18 | 18 | 18 | 18 | 18 | 16 |
| Distribution of sulfonate group (% by mass) | (IO-1S) | Position 1 | 1.6 | 1.5 | 1.4 | 1.4 | 1.3 | 1.1 | 1 | 0.9 | 0.7 | 0.6 | 1.5 |
| | | Position 2 | 31.5 | 25.9 | 24 | 22.1 | 20.6 | 19 | 17.4 | 15.9 | 14.4 | 12.8 | 24.1 |
| | | Position 3 | 25.1 | 20.4 | 18.8 | 17.2 | 16.1 | 15 | 14 | 12.9 | 11.8 | 10.7 | 19.9 |
| | | Position 4 | 24.7 | 23 | 22.4 | 21.8 | 20.9 | 20.1 | 19.2 | 18.3 | 17.5 | 16.6 | 24.6 |
| | (IO-2S) | Positions 5 to 9 | 17.1 | 29.2 | 33.4 | 37.5 | 41.1 | 44.8 | 48.4 | 52 | 55.6 | 59.3 | 29.9 |
| | | Total | 100 | 100 | 100 | 100 | 100 | 100 | 100 | 100 | 100 | 100 | 100 |
| (IO-1S)/(IO-2S) (mass ratio) | | | 4.8 | 2.4 | 2.0 | 1.6 | 1.4 | 1.2 | 1.0 | 0.91 | 0.79 | 0.68 | 2.3 |

<Components to be Blended>
[Component (A)]
It was selected from Table 4 and used. [Component (A')] (comparative component of component (A))
(a'-1) or (a'-2) in Table 4 was used. [Component (B)]
Component (b-1): phenoxyethanol (C log P=1.2) [an organic solvent of the above-mentioned component (B4)]
Component (b-2): diethylene glycol monobutyl ether (C log P=0.67) [an organic solvent of the above-mentioned component (B3)]
Component (b-3): ethanol (C log P=−0.24) [an organic solvent of the above-mentioned component (B1)]
Component (b-4): propylene glycol (C log P=−1.1) an [organic solvent of the above-mentioned component (B2)]
Component (b-5): glycerol (C log P=−1.5) [an organic solvent of the above-mentioned component (B2)]
Component (b-6): dipropylene glycol monoethyl ether (C log P=0.23) [an organic solvent of the above-mentioned component (B3)]
[Water]
Ion-Exchanged Water
<Preparation of Liquid Detergent Composition for Textile Products>
Liquid detergent composition for textile products shown in Tables 5 to 7 were prepared using the above-mentioned components to be blended, and were evaluated for the following items. The results are shown in Tables 5 to 7.

Specifically, the liquid detergent composition for textile products shown in Tables 5 to 7 was as follows. A Teflon® stirrer piece having a length of 5 cm was placed in a 200 mL glass beaker and its mass was measured. Next, 80 g of ion-exchanged water at 20° C., component (A) or component (A'), and component (B) were introduced thereinto, and the beaker was sealed at its top side with Saran wrap®.

The beaker containing the contents was placed in a water bath at 60° C. placed on a magnetic stirrer, and stirred at 100 r/min for 30 minutes at a water temperature range in the water bath of 60±2° C. Next, the water in the water bath was replaced with tap water at 5° C. and cooled until the temperature of the composition in the beaker was 20° C. Next, Saran Wrap® was removed, ion-exchanged water was added so that the mass of the contents was 100 g and stirred again at 100 r/min for 30 seconds to obtain each of the liquid detergent composition for textile products shown in Tables 5 to 7.
<Evaluation Method of Softness>
(1) Pretreatment of Textile Products to be Evaluated
1.7 kg of knitted cotton (un-mercerized knitted cotton (not mercerized one), cotton 100%, manufactured by Shikisensha Co., Ltd.) was previously washed cumulatively twice with a standard course of a fully automatic washing machine (NA-F702 P manufactured by Matsushita Electric Industrial Co., Ltd.) (4.7 g of Emulgen 108 (manufactured by Kao Corporation) at washing; the amount of water: 47 L; washing for 9 minutes, rinsing twice and spin-drying for 3 minutes) followed by cumulatively washing three times with water only (the amount of water: 47 L; washing for 9 minutes, rinsing twice and spin-drying for 3 minutes), and dried under an environment of 23° C. and 45% RH for 24 hours.
(2) Washing of Textile Products to be Evaluated
(2-1) Method (1)
6.0 L of municipal water (3.5° dH) the temperature of which was adjusted to 5° C. was poured into an electric bucket type washing machine (model number "N-BK2", manufactured by Matsushita Electric Industrial Co., Ltd. (presently Panasonic Corporation)), and four cut pieces of knitted cotton (approximately 140 g) which had been pretreated by the above-mentioned method were then introduced thereinto. Next, each of the liquid detergent compositions for textile products listed in Tables 5 and 6 was introduced thereinto so that the concentration of component (A) in the bath was 200 mg/kg, and washed for 10 minutes. After washing, spin-drying was carried out for 1 minute using a two-compartment washing machine (model number: "PS-H35L", manufactured by Hitachi, Ltd.). Next, 6.0 L of municipal water at 5° C. was poured into the bucket type washing machine, and a cotton towel after spin-dried with the two-compartment washing machine manufactured by Hitachi, Ltd. was introduced thereinto and rinsed for 3 minutes. Thereafter, it was subjected to the same spin-drying for 1 minute with the two-compartment washing machine, and was allowed to stand for 12 hours under the conditions of 20° C. and 43% RH to dry it.
(2-2) Method (2)
6.0 L of municipal water (3.5° dH) the temperature of which was adjusted to 5° C. was poured into an electric bucket type washing machine (model number "N-BK 2", manufactured by Matsushita Electric Industrial Co., Ltd. (presently Panasonic Corporation)). Each of the liquid detergent compositions for textile products listed in Table 7 was sprinkled on and thereby attached to four cut pieces of knitted cotton (approximately 140 g) which had been pretreated by the above-mentioned method so that the concentration of component (A) in the bath was 200 mg/kg. The cut pieces of knitted cotton to which each of the liquid detergent compositions for textile products listed in Table 7 was attached were introduced into in the washing machine and washed for 10 minutes. After washing, they were subjected to spin-drying for 1 minute with a two-compartment washing machine (model number: "PS-H35L", manufactured by Hitachi, Ltd.). Next, 6.0 L of the municipal water at 5° C. was poured into the bucket type washing machine, and a cotton towel after spin-dried with the two-compartment washing machine (manufactured by Hitachi, Ltd.) was introduced into the bucket type washing machine and rinsed for 3 minutes. Thereafter, it was subjected to the same spin-drying for 1 minute with the two-compartment washing machine, and was allowed to stand for 12 hours under the conditions of 20° C. and 43% RH to dry it.

(3) Evaluation of Softness

The softness of the knitted cotton after drying was scored according to the following criteria by six experts skilled in the texture evaluation of fibers, and the average score of the scores of six experts was calculated by rounding it off to three significant digits. In scoring, for example, when it was evaluated as corresponding to the score between 2 and 3, it was given score 2.5.

−1 . . . It was not finished more softly than the knitted cotton treated with the composition of Comparative Example 1.

0 . . . It was finished as softly as the knitted cotton treated with the composition of Reference 1.

1 . . . It was finished somewhat more softly than the knitted cotton treated with the composition of Reference 1.

2 . . . It was finished more softly than the knitted cotton treated with the composition of Reference 1.

3 . . . It was finished as softly as the knitted cotton treated with the composition of Reference 2.

Table 5 shows the evaluation using the composition of Comparative Example 3 as reference 1 and the composition of Example 1 as reference 2. Table 6 shows the evaluation using the composition of Comparative Example 3 as reference 1 and the composition of Example 8 as reference 2. Table 7 shows the evaluation using the composition of Comparative Example 3 as reference 1 and the composition of Example 15 as reference 2. Furthermore, the average score obtained was normalized by the relative value obtained by setting the score 3 according to the above criteria (the score of reference 2) to score 10. When the normalized value was smaller than 0 (reference 1), it was given "−1". The results are shown in Tables 5, 6 and 7.

<Evaluation Method of Detergent Property>

(1) Preparation of the Model Artificially Sebum-Stained Cloth

A model artificially sebum-stained cloth was prepared by applying a model artificially sebum-staining liquid of the following composition to a cloth. The application of the model artificially sebum-staining liquid to the cloth was carried out by printing the artificially staining liquid on the cloth using a gravure roll coater. The process for preparing the model artificially sebum-stained cloth by applying the model artificially sebum-staining liquid to the cloth was carried out with a cell capacity of the gravure roll of 58 $cm^3/m^2$, a coating speed of 1.0 m/min, a drying temperature of 100° C. and a drying time of 1 minute. The cloth used was Cotton 2003 (manufactured by Tanigashira Shoten).

The composition of the model artificially sebum-staining liquid: Laurie acid: 0.4% by mass, myristic acid: 3.1% by mass, pentadecanoic acid: 2.3% by mass, palmitic acid: 6.2% by mass, heptadecanoic acid: 0.4% by mass, stearic acid: 1.6% by mass, oleic acid: 7.8% by mass, triolein: 13.0% by mass, n-hexadecyl palmitate: 2.2% by mass, squalene: 6.5% by mass, egg white lecithin liquid crystal product: 1.9% by mass, Kanuma red clay: 8.1% by mass, carbon black: 0.01% by mass and water: balance (total 100% by mass).

(2) Evaluation of Detergency

Five cut pieces of the model artificially sebum-stained cloth (6 cm×6 cm) as prepared above were washed at 85 rpm in Terg-O-Tometer (MS-8212, manufactured by Ueshima Seisakusho Co., Ltd.) for ten minutes. For washing conditions, washing was carried out at a water temperature of 20° C. by pouring municipal water (3.5° dH, 20° C.) so that each of the concentrations of the liquid detergent composition for textile products shown in Table 5 was 0.033% by mass. After washing, rinsing with municipal water (20° C.) was carried out for 3 minutes. The washing percentage (%) was measured by the following method, and the average value of washing percentages of the five cut pieces was determined. The results are shown in Table 5. The reflectance at 550 nm of each of the original cloth before staining and the clothes before and after washing was measured with a differential colorimeter (Z-300A, manufactured by Nippon Denshoku Industries Co., Ltd.).

Washing percentage (%)=100×[(reflectance after washing−reflectance before washing)/(reflectance of original cloth−reflectance before washing)]

TABLE 5

|  |  |  |  | Example |  |  |  |  |  |  | Comparative Example |  |  |
|---|---|---|---|---|---|---|---|---|---|---|---|---|---|
|  |  |  |  | 1 | 2 | 3 | 4 | 5 | 6 | 7 | 1 | 2 | 3 |
| Detergent composition for textile products | Content (% by mass) | (A) | (a-1) | 15 |  |  |  |  |  |  |  |  |  |
|  |  |  | (a-3) |  | 15 |  |  |  |  |  |  |  |  |
|  |  |  | (a-4) |  |  | 15 |  |  |  |  |  |  | 15 |
|  |  |  | (a-5) |  |  |  | 15 |  |  |  |  |  |  |
|  |  |  | (a-7) |  |  |  |  | 15 |  |  |  |  |  |
|  |  |  | (a-8) |  |  |  |  |  | 15 |  |  |  |  |
|  |  |  | (a-9) |  |  |  |  |  |  | 15 |  |  |  |
|  |  | (A') | (a'-1) |  |  |  |  |  |  |  | 15 |  |  |
|  |  |  | (a'-2) |  |  |  |  |  |  |  |  | 15 |  |
|  |  | (B) | (b-1) | 10 | 10 | 10 | 10 | 10 | 10 | 10 | 10 | 10 |  |
|  |  | Ion-exchanged water |  | Balance | Balance | Balance | Balance | Balance | Balance | Balance | Balance | Balance | Balance |
|  |  | Total |  | 100 | 100 | 100 | 100 | 100 | 100 | 100 | 100 | 100 | 100 |
|  |  | (IO-1)/(IO-2) (mass ratio)[1] |  | 6.2 | 1.8 | 1.4 | 1.2 | 0.80 | 0.66 | 0.54 | 0.44 | 2.2 | 1.4 |
|  |  | (IO-1S)/(IO-2S) (mass ratio)[2] |  | 4.8 | 2.0 | 1.6 | 1.4 | 1.0 | 0.91 | 0.79 | 0.68 | 2.3 | 1.6 |

TABLE 5-continued

|  |  | Example |  |  |  |  |  |  | Comparative Example |  |  |
|---|---|---|---|---|---|---|---|---|---|---|---|
|  |  | 1 | 2 | 3 | 4 | 5 | 6 | 7 | 1 | 2 | 3 |
|  | Content of component (B)/ content of component (A) (mass ratio) | 0.67 | 0.67 | 0.67 | 0.67 | 0.67 | 0.67 | 0.67 | — | — | — |
| Evaluation results | washing percentage (%) | 31 | 33 | 33 | 28 | 25 | 23 | 22 | 21 | 32 | 33 |
|  | Softness | 10 (Reference 2) | 9.7 | 9.4 | 9.2 | 8.9 | 8.6 | 8.3 | 8.1 | −1 | 0 (Reference 1) |

(1) Mass ratio of (IO-1)/(IO-2) in an olefin as a raw material
(2) Mass ratio of (IO-1S)/(IO-2S) in an internal olefin sulfonate

TABLE 6

|  |  |  |  |  | Example |  |  |  |  |  | Comparative Example |
|---|---|---|---|---|---|---|---|---|---|---|---|
|  |  |  |  |  | 8 | 9 | 10 | 11 | 12 | 13 | 14 | 3 |
| Detergent composition for textile products | Content (% by mass) | (A) | | (a-4) | 15 | 15 | 15 | 15 | 15 | 25 | 25 | 15 |
|  |  | (B) | (b-1) | ClogP = 1.2 | 4.8 |  |  |  |  |  | 8 |  |
|  |  |  | (b-2) | ClogP = 0.67 |  | 4.8 |  |  |  | 8 |  |  |
|  |  |  | (b-3) | ClogP = −0.24 |  |  | 4.8 |  |  |  |  |  |
|  |  |  | (b-4) | ClogP = −1.1 |  |  |  | 4.8 |  |  |  |  |
|  |  |  | (b-5) | ClogP = −1.5 |  |  |  |  | 4.8 |  |  |  |
|  |  |  | Ion-exchanged water |  | Balance | Balance | Balance | Balance | Balance | Balance | Balance | Balance |
|  |  |  | Total |  | 100 | 100 | 100 | 100 | 100 | 100 | 100 | 100 |
|  | Content of component (B)/content of component (A) (mass ratio) |  |  |  | 0.32 | 0.32 | 0.32 | 0.32 | 0.32 | 0.32 | 0.32 | — |
| Evaluation results |  |  | Softness |  | 10 (Reference 2) | 10 | 10 | 10 | 10 | 10 | 10 | 0 (Reference 1) |

TABLE 7

|  |  |  |  |  | Example |  |  |  |  |  | Comparative Example |
|---|---|---|---|---|---|---|---|---|---|---|---|
|  |  |  |  |  | 15 | 16 | 17 | 18 | 19 | 20 | 3 |
| Detergent composition for textile products | Content (% by mass) | (A) | | (a-3) | 20 | 20 | 20 | 20 | 20 | 20 | 15 |
|  |  | (B) | (b-1) | ClogP = 1.2 | 8 |  |  |  | 3 | 5 |  |
|  |  |  | (b-2) | ClogP = 0.67 |  | 8 |  |  | 5 |  |  |
|  |  |  | (b-6) | ClogP = 0.23 |  |  | 8 |  |  |  |  |
|  |  |  | (b-4) | ClogP = −1.1 |  |  |  | 8 |  | 3 |  |
|  |  |  | Ion-exchanged water |  | Balance | Balance | Balance | Balance | Balance | Balance | Balance |
|  |  |  | Total |  | 100 | 100 | 100 | 100 | 100 | 100 | 100 |
|  | Content of component (B)/content of component (A) (mass ratio) |  |  |  | 0.4 | 0.4 | 0.4 | 0.4 | 0.4 | 0.4 | — |
| Evaluation results |  |  | Softness |  | 10 (Reference 2) | 10 | 9.2 | 8.5 | 10 | 9.2 | 0 (Reference 1) |

The invention claimed is:

1. A liquid detergent composition for textile products comprising:

10% by mass or more and 60% by mass or less of component (A): an internal olefin sulfonate having 18 or more and 24 or less carbon atoms, wherein a mass ratio of an internal olefin sulfonate having 18 or more and 24 or less carbon atoms with the sulfonate group at position 2 or higher and position 4 or lower (IO-1S) to an internal olefin sulfonate having 18 or more and 24 or less carbon atoms with the sulfonate group at position 5 or higher (IO-2S), (IO-1S)/(IO-2S), is 1.0 or more and 5.5 or less;

component (B): an organic solvent having a hydroxy group, wherein ClogP of component (B) is −0.1 or more and 2 or less; and water.

2. The liquid detergent composition for textile products according to claim 1, wherein (IO-2S) is an internal olefin sulfonate having 17 or more and 24 or less carbon atoms with the sulfonate group at position 5 or higher and position 9 or lower.

3. The liquid detergent composition for textile products according to claim 1, wherein the content of (IO-2S) in the component (A) is 60% by mass or less and more than 0% by mass.

4. The liquid detergent composition for textile products according to claim 1, wherein a percentage of the component (A) in all anionic surfactants contained in the liquid detergent composition for textile products is 60% by mass or more and 100% by mass or less.

5. The liquid detergent composition for textile products according to claim 1, wherein the content of the component (B) is 4% by mass or more and 35% by mass or less.

6. The liquid detergent composition for textile products according to claim 1, wherein content of component (B)/content of component (A), which is a mass ratio of the content of the component (B) to the content of the component (A) is 0.1 or more and 1 or less.

7. The liquid detergent composition for textile products according to claim 1, wherein the component (B) is one or more selected from the following components (B1) to (B4):
component (B1): a monohydric alcohol having 2 or more and 6 or less carbon atoms;
component (B2): an alcohol having 2 or more and 12 or less carbon atoms and 2 or more and 12 or less hydroxy groups;
component (B3): an organic solvent having a hydrocarbon group with 1 or more and 8 or less carbon atoms, an ether group and a hydroxy group (provided that an aromatic group is excluded from the hydrocarbon group); and
component (B4): an organic solvent having an optionally partially substituted aromatic group, an ether group and a hydroxy group.

8. The liquid detergent composition for textile products according to claim 7, wherein the percentage of the content of the organic solvent selected from the component (B3) and the component (B4) and having the ClogP of 0.6 or more and 1.5 or less in the overall component (B) is 40% by mass or more and 100% by mass or less.

9. The liquid detergent composition for textile products according to claim 7, wherein the monohydric alcohol having 2 or more and 6 or less carbon atoms which is the component (B1) is a compound selected from ethanol, 1-propanol and 2-propanol.

10. The liquid detergent composition for textile products according to claim 7, wherein the alcohol having 2 or more and 12 or less carbon atoms and 2 or more and 12 or less hydroxy groups which is the component (B2) is hexylene glycol.

11. The liquid detergent composition for textile products according to claim 7, wherein the organic solvent having a hydrocarbon group having 1 or more and 8 or less carbon atoms, an ether group and a hydroxy group which is the component (B3) is a compound selected from diethylene glycol dimethyl ether, diethylene glycol monoethyl ether, dipropylene glycol monomethyl ether, dipropylene glycol monoethyl ether, tripropylene glycol monomethyl ether, 1-methoxy-2-propanol, 1-ethoxy-2-propanol, 1,3-dimethyl glycerol ether, 1,3-diethyl glycerol ether, triethyl glycerol ether, 1-pentyl glyceryl ether, 2-pentyl glyceryl ether, 1-octyl glyceryl ether, and 2-ethylhexyl glyceryl ether.

12. The liquid detergent composition for textile products according to claim 7, wherein the organic solvent having an optionally partially substituted aromatic group, an ether group and a hydroxy group which is the component (B4) is a compound selected from 2-phenoxyethanol, diethylene glycol monophenyl ether, triethylene glycol monophenyl ether, 2-benzyloxy ethanol and diethylene glycol monobenzyl ether.

13. The liquid detergent composition for textile products according to claim 1, wherein the content of water is 10% by mass or more and 80% by mass or less.

14. A method for producing a liquid detergent composition for textile products, comprising mixing the following component (A), the following component (B), and water, wherein a percentage of the component (A) in all components to be mixed is 10% by mass or more and 60% by mass or less:
component (A): an internal olefin sulfonate having 18 or more and 24 or less carbon atoms, wherein a mass ratio of an internal olefin sulfonate having 18 or more and 24 or less carbon atoms with the sulfonate group at position 2 or higher and position 4 or lower (IO-1S) to an internal olefin sulfonate having 18 or more and 24 or less carbon atoms with the sulfonate group at position 5 or higher (IO-2S), (IO-1S)/(IO-2S), is 1.0 or more and 5.5 or less; and
component (B): an organic solvent having a hydroxy group, wherein ClogP of component (B) is −0.1 or more and 2 or less.

15. A method for producing a liquid detergent composition for textile products, including mixing the following component (A1), the following component (B) and water, wherein a percentage of the component (A1) in all components to be mixed is 10% by mass or more and 60% by mass or less:
component (A1): an internal olefin sulfonate obtained from an internal olefin having 18 or more and 24 or less carbon atoms, wherein a mass ratio of an olefin having 18 or more and 24 or less carbon atoms with a double bond at position 1 or higher and position 3 or lower (IO-1) to an olefin having 18 or more and 24 or less carbon atoms with a double bond at position 5 or higher (IO-2), (IO-1)/(IO-2) is 0.50 or more and 6.5 or less; and
component (B): an organic solvent having a hydroxy group, wherein ClogP of component (B) is −0.1 or more and 2 or less.

16. A method for washing textile products, including washing the textile products with a detergent liquid containing the liquid detergent composition for textile products according to claim 1, and water.

17. The method for washing textile products according to claim 16, wherein the content of the component (A) in the detergent liquid is 0.005% by mass or more and 1.0% by mass or less.

18. The method for washing textile products according to claim 16, wherein the content of the component (B) in the detergent liquid is 0.001% by mass or more and 0.8% by mass or less.

* * * * *